United States Patent
Nile et al.

Patent Number: 5,570,475
Date of Patent: Nov. 5, 1996

[54] SURGEON'S GLOVE HAVING IMPROVED DONNING PROPERTIES

[75] Inventors: Jeffery G. Nile, Alliance; Stanley J. Gromelski, Canton, both of Ohio; Alan A. Brain, Harlow; Steven T. Hardwick, Watford, both of England

[73] Assignee: Ansell Perry Inc., Massillon, Ohio

[21] Appl. No.: 424,561

[22] Filed: Apr. 17, 1995

Related U.S. Application Data

[63] Continuation of Ser. No. 307,024, Sep. 14, 1994, abandoned, which is a continuation of Ser. No. 957,983, Oct. 8, 1992, abandoned, which is a continuation-in-part of Ser. No. 776,084, Oct. 11, 1991, abandoned.

[51] Int. Cl.$^6$ .................................................. A41D 19/00
[52] U.S. Cl. ........................... 2/161.7; 2/161.8; 2/167; 2/168; 428/424.2; 428/424.4; 428/492; 428/494; 428/495; 428/516; 428/517; 428/520
[58] Field of Search ................................ 2/161.7, 161.8, 2/167, 168; 428/424.2, 424.4, 492, 494, 495, 516, 517, 520

[56] References Cited

U.S. PATENT DOCUMENTS

| | | | |
|---|---|---|---|
| 3,856,561 | 12/1974 | Esemplare et al. | 117/139 |
| 3,879,496 | 4/1975 | Paxton | 525/305 |
| 4,070,713 | 1/1978 | Stockum | 2/168 |
| 4,330,597 | 5/1982 | Heins et al. | 428/473 |
| 4,499,154 | 2/1985 | James et al. | 428/494 |
| 4,507,342 | 3/1985 | Kielbanra, Jr. | 428/90 |
| 4,879,348 | 11/1989 | Henton | 428/473 |

*Primary Examiner*—D. S. Nakarani
*Attorney, Agent, or Firm*—Gardner, Carton & Douglas

[57] ABSTRACT

There is disclosed a body contacting article, eg. a surgeon's glove which comprises a first layer of a natural or synthetic elastomer and thereupon a layer of polymer comprising repeating units of the formula:

$$[-CH_2-CH(OR)-] \text{ and } [-CH(CO_2H)-CH(CO_2R^1)-] \quad (I)$$

$$[-CH_2-CH(R^4)-] \text{ and } [-CH(CO_2H)-CH(CO_2R^1)-] \quad (IA)$$

wherein R is a lower alkyl group and $R^1$ is a lower alkyl group or a (lower) alkoxy (low) alkyl group, and $R^4$ is hydrogen or a phenyl group.

8 Claims, 3 Drawing Sheets

SURGEON'S GLOVE HAVING IMPROVED DONNING PROPERTIES

This is a continuation of our application Ser. No. 08/307,024, filed Sep. 14, 1994, now abandoned, which is a continuation of our application 07/957,983, filed Oct. 8, 1992, now abandoned, which is a continuation-in-part of our application Ser. No. 08/776,084, filed Oct. 11, 1991, now abandoned.

This invention relates to body contacting articles fabricated from natural or synthetic elastomeric materials e.g. natural or synthetic rubbers or polyurethanes. More particularly, the invention relates to medicinal gloves and especially to surgeon's gloves.

In order to improve the donning properties of gloves such as thin rubber or polyurethane gloves of the type used in medical examinations or surgical procedures, it has been customary to incorporate a donning aid at least at the hand contacting surface of the glove. Conventional donning aids have been powders such as talc or starch. However, the use of such particulate donning aids has the disadvantage that particles may drop off the glove into the wound possibly resulting in a granuloma. In order to avoid the use of donning powders other attempts to improve the donning properties of the glove have included the treatment of the hand contacting surface of the glove by halogenation or by lamination with another material having better donning properties than the base rubber. Other articles of natural or synthetic elastomeric materials also suffer problems associated with application due to the frictional resistance of the natural or synthetic elastomeric material employed in the manufacture of the article and the body portion with which it is to be contacted.

Delamination caused during stretching or flexing of the glove has been a problem associated with such laminated gloves particularly when the glove is donned when the hands are wet.

Attempts to improve resistance to delamination have included treatment of the natural or synthetic elastomeric base material surface for example by acid priming so that the laminated material keys well to the base material and remains adhered whilst the base material is stressed. In U.S. Pat. No. 4499154 there is disclosed a process for producing a flexible rubber article in which the formed rubber article is subjected to an acid priming step and a neutralising step prior to a polymer coating step.

The present invention seeks to mitigate the disadvantages of the prior art and to provide body contacting articles such as surgeon's gloves having good donning properties, by using polymers which can be applied directly to the natural or synthetic elastomeric surface without the necessity of pretreating that surface.

Thus the present invention provides a process which is simpler and more economical than those hitherto known.

Figure 1:
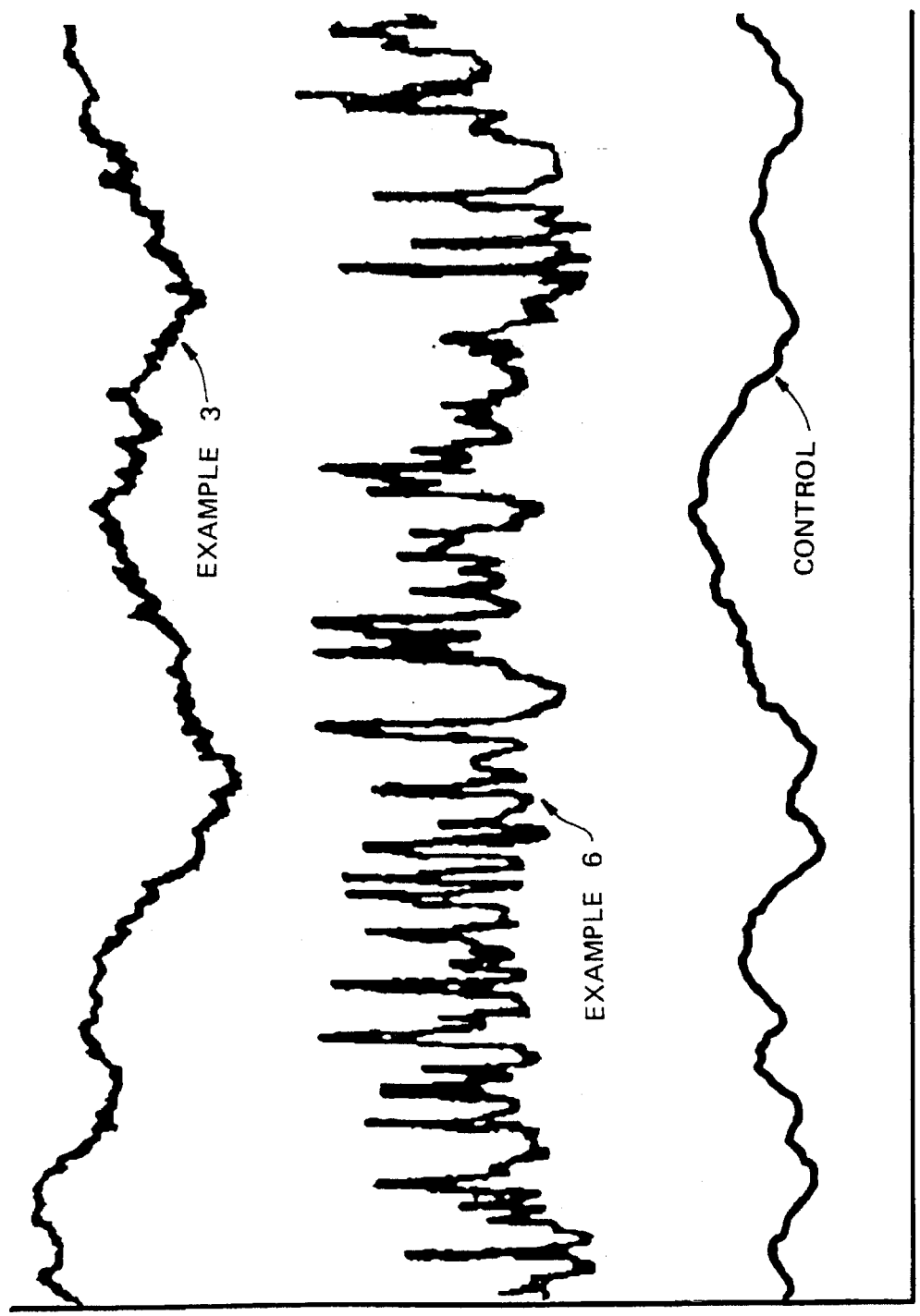
FIG. 1 depicts the surface morphology of gloves according to the invention.

According to the present invention there is provided a body contacting article which comprises a first layer of a natural or synthetic elastomer and thereon a layer of a polymer comprising repeating units of the formula:

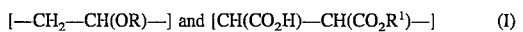
    (I)

or

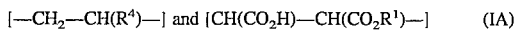
    (IA)

wherein R is a lower alkyl group and $R^1$ is a lower alkyl group or a (lower) alkoxy (lower) alkyl group, and $R^4$ is hydrogen or a phenyl group.

Aptly R is a lower alkyl group containing up to 4 carbon atoms. More suitably R is a methyl group. Aptly $R^1$ is a lower alkyl group containing up to 9 carbon atoms (e.g. methyl, propyl, butyl, pentyl, hexyl, octyl or nonyl) more aptly up to 4 carbon atoms; or an alkoxy alkyl group having up to 4 carbon atoms in the alkoxy part and up to 4 carbon atoms in the alkyl part (eg. a propoxyethyl group). Suitably, when R is a methyl group, $R^1$ is a propyl or butyl group. More suitably $R^1$ is a $-(CH_2)_3CH_3$ group.

The natural or synthetic elastomer preferably comprises a natural rubber or a polychloroprene (e.g. Neoprene), a nitrile rubber, a styrene butadiene rubber or a polyurethane.

The polymers for use in the polymer layer favourably comprise or consist essentially of repeating units of formula (I) or (IA). Such polymers may be referred to as copolymers of a vinyl alkyl ether and a maleic ester (I), or of an alkylene and a maleic ester (IA).

Preferably the body contacting article is a surgeon's glove.

According to a further embodiment of the invention there is also provided a surgeon's glove which comprises a rubber glove which has on the hand contacting surface thereof a layer of a polymer comprising repeating units of the formula:

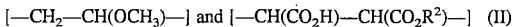
    (II)

wherein $R^2$ is lower alkyl group. Suitably $R^2$ is an alkyl group containing up to 9 carbon atoms, more suitably up to 4 carbon atoms. Preferably $R^2$ is a propyl or butyl group. More preferably $R^2$ is an n-butyl or a $-(CH_2)_3CH_3$ group.

The preferred polymers for use in the polymer layer favourably comprise or consist essentially of repeating units of the formula II. Such polymers may be referred to as copolymers of vinyl methyl ether and a maleic ester.

Polymers having repeating units of formula I or II are commercially available and are sold under the trade name GANTREZ (available from GAF Corporation). Apt polymers are those of the GANTREZ ES series of resins and are described as alkyl monoesters of poly(methyl vinyl ether - maleic acid). Suitable resins of this series are the isoproply and n-butyl esters sold under the trade names ES-335, ES-425 and ES435.

Other polymers may however be suitable and these includes polymers of;

(i) the butyl half ester of poly(ethylene/maleic acid)—which is a rubbery material that laminates satisfactorily to rubber.

(ii) the butyl half ester of Scripset 520 (butyl half ester of poly (Styrene/maleic acid) which is a glassy material.

(iii) SMA 2625 (partly esterified poly(styrene/maleic acid))—which is a glassy material that laminates satisfactorily to rubber.

(Scripset 520 is a trade mark and relates to a substance obtainable from Monsanto).

The polymers having repeating units of formula I, IA or II may be applied directly to formed articles having a natural or synthetic elastomer surface.

Accordingly therefore there is also provided a method for producing a body contacting article comprising a first layer of a natural or synthetic elastomeric material, which method comprises applying to said first layer a layer of a polymer having repeating units of the formula I, IA or II as hereinabove defined.

The method of the present invention may be employed as part of the article manufacturing process. For example, where the article is a glove such as a surgeon's glove, the glove may be first formed by a conventional dipping procedure wherein a suitably shaped former is first dipped into a coagulant and thereafter into a latex solution comprising the natural or synthetic elastomer, e.g. natural rubber from which the article is to be formed. After withdrawal from the dipping bath the article may then be subjected to a conventional washing or leaching step prior to application of the polymer layer.

In a preferred aspect of the process of the present invention the formation of the polymer layer on the natural or synthetic elastomer surface takes place prior to final curing of the elastomer. Thus in a conventional glove dipping process, the process train may be modified by incorporating the process of the invention as an intermediate step between the leaching and curing steps.

Thus in accordance with an embodiment of the invention there is provided a process for the production of dipped articles in which a layer of a polymer having repeating units of formula (I), (IA) or (II) is applied to a natural or synthetic eastomer surface of the article prior to final curing of the rubber article.

Aptly, the polymer may be applied to the elastomer surface as a solution. Suitably the solution employed is an alcoholic solution. Preferred alcohols for forming the polymer solution include alkanols such as ethanol and isopropanol.

The polymer content in such solutions should not be more than 50% by weight of the solution, aptly up to about 15% by weight of the total solution, and preferably up to about 8% by weight. Generally, the polymer contact of the solution will be at least 2% by weight of polymer. Preferably polymer contents of from 4 to 6% by weight may be used.

The elastomers can be obtained as latices, which can then be dipped and coated. Cosolvents can be used in the preparation of the latices and the elastomer may be initially present in an emulsion, e.g. a polyurethane emulsion.

The polymer layer may be formed by conventional solution coating procedures but is aptly formed by dipping the article into a solution of the polymer.

The polymer solution may be employed at temperatures below the boiling range of the polymer solvent and may suitably be used at ambient temperatures.

Although the polymer may be used alone, additional hydroxyl containing compounds may be added to the polymer solution. Aptly such hydroxyl containing compounds may include water or polyhydroxy compounds such as polyethylene glycol.

Aptly water may be present in the polymer solution in amounts up to 50% by weight based upon the weight of the solution.

Preferred polyethylene glycols for inclusion with polymers having repeating units of formula (I), (IA) or (II) are those commercially available under the tradename CARBOWAX. Polyhydroxy compounds, as typified by the carbowaxes, may be present in amounts up to about 30% by weight of the polymer aptly in amounts up to 10%, possibly up to 5%, up to 1% or up to 0.5% by weight of the polymer.

After application of the polymer layer, the article may be dried and cured according to conventional procedures.

The article may thereafter be subjected to post-curing treatments such as halogenation in order to impart desired physical properties to the product.

We have found that further improvements in the hand donning properties may be obtained by treatment with an agent such as a surfactant. An apt surfactant for use with the invention is cetyl pyridinium chloride (CPC). Although this surfactant may be employed alone, it may suitably be employed as a complex with a long chain acid, more suitably with a fatty acid. Preferred fatty acids include stearic acid. Lauric acid is especially preferred. CPC in admixture with fatty acid derivatives such as lauryl sulphonate may also be used but these mixtures are less preferred.

Suitable complexes may be formed by adding each of the constituents to water and applying the aqueous complex to the article. A preferred complex may be formed by admixing CPC and lauric acid in water and heating such that each constituent is present in amounts of about 2% by weight of the aqueous complex.

The complex may be applied either by spraying it onto the elastomer surface of the article or by immersing the article in the aqueous complex. Suitably the complex is applied at elevated temperature. Spraying is preferred. In a preferred embodiment the spraying is carried out at elevated temperature, aptly at about 130° F. Dipping applications may be carried out at temperatures of about 100° F.

Other donning aids such as silicones used either along or in combination wit the CPC containing complexes may also be used with advantage.

Thereafter the treated article is dried.

Examination of the elastomer surface and the polymer layer thereon, for example by a Scanning Electron Microscope (SEM) shows the polymer to be distributed over the whole of the rubber surface.

The articles of the invention may have flat polymer coatings. However, in preferred form of the invention, the polymer layer, whilst being continuous has raised areas (domains) which are thicker than the surrounding polymer layer. In these preferred forms of the invention the thickness of the raised domains may be up to 25 μm thicker than that of the remaining areas, favourably up to about 7 μm thicker. The remaining areas may be less than about 8 μm thickness, aptly between 6 and 7 μm, more aptly less than 1 μm The occurrence of raised domain architecture of the polymer surface depends mainly upon the condition of the elastomer surface to which the polymer is applied.

We have found that if the elastomer surface contains moisture, for example after the leaching stage in a conventional dipping process train, a raised domain architecture will occur when the polymer is applied. Thus it is preferred to apply the polymer between the leaching and curing stages when the articles are produced by a dipping process.

Further improvements in the donning preparation of articles such as gloves when produced in accordance with the invention have been determined when a polymer has repeating units of the formula

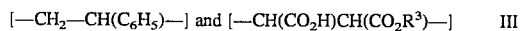

[—CH$_2$—CH(C$_6$H$_5$)—] and [—CH(CO$_2$H)CH(CO$_2$R$^3$)—]  III where R$^3$ is an alkyl group. Aptly R$^3$ is a lower alkyl group, more aptly R$^3$ is an alkyl group, containing up to 4 carbon atoms. Suitable polymers having repeating units of formula (III) are sold under the trade name SCRIPSETS (available from Monsanto). Preferred grades are those sold under the designations SCRIPSETS 540 and SCRIPSETS 550.

Other similar and suitable polymers may be those sold under the trade name SMA resin (available for Atochem) e.g. the polymer sold under the trade name SMA 2625, which is effective in combination with the polymers having repeating units of formula I and II.

Polymers having repeating units of formula (III) may be incorporated directly into the solution of the polymer having repeating units of formula (I), (IA) or (II). Aptly polymer (III) may present in the polymer (II) solution in an amount of greater than about 5% by weight of the total solids content of the solution. Preferably the concentration of polymer III will be about 20% by weight or less of the solution solids. In favoured form the solution for forming the polymer layer on the article will comprise or consist essentially of 94% by weight of ethanol, 4.8% by weight of a polymer having repeating units of formula (I) or (IA) and 1.2% be weight of a polymer having repeating units of formula (III).

The surface morphology of articles having the above described modified polymer layer shows that the raised areas have further raised areas thereon.

Gloves produced with said modified layers have good donning properties especially wet hand donning properties.

In addition to having the modified polymer layer thereon, the donning properties body contact articles may further improve by the use of donning aids, for example as hereinbefore described.

The invention will now be illustrated by the following examples.

EXAMPLE 1

An alcoholic coagulant solution was prepared according to the formulation:

| Industrial Methylated Spirits | 3469 lbs |
|---|---|
| Calcium Nitrate | 71 gals (US) |
| Triton X-100 | 1.153 Kg |
| Carbowax 600 | 17.7 lbs |
| Calcium Carbonate | 250 lbs |
| Surfynol TG (An acetylenic surfactant) | 450.2 gm |

Glove formers, for moulding a surgeon's glove, were immersed in the coagulant solution for 1 minute. The temperature of the coagulated solution was maintained at 110° F.

The coagulant treated former was then dipped into a latex solution for 1 minute. The temperature of the latex was ambient temperature and the solution had the following composition:

| Water | 3600 lbs |
|---|---|
| Natural rubber Latex | 9750 lbs |
| Modicol (elemental sulphur dispersion) | 3 lbs |
| DPTT[1] Dispersion | 210 lbs |
| ZMBT[2] Dispersion | 46 lbs |
| MZ[3] Dispersion | 30 lbs |
| Lowinox[4] Dispersion | 148 lbs |

[1]Dipentylmethylene thiuram tetrasulphide
[2]Zinc Mercaptobenzathiazole
[3]Methyl Zimate
[4]a hindered phenol antioxidant.

The final solids content of the latex solution was reduced by the addition of a further 800 lbs of water.

Upon removal from the latex solution the coated formers are then immersed in a leaching bath, maintained at 160° F., for 2 minutes.

The leached coated formers were immersed in a polymer bath, maintained at ambient temperature before passage to a curing oven where they were dried at 240° F. for 20 minutes.

The polymer solution was prepared by diluting an ethanolic solution of GANTREZ ES-425 copolymer to 4% by weight solids content with industrial methylated spirits.

GANTREZ ES-425 has repeating units of Formula (II) in which $R^2$ is a $(CH_2)_3CH_3$ group. To the 4% resin solution was added a polyethylene glycol (Carbowax 600) in an amount of 20% by weight based on the weight of the resin.

After curing all the gloves were removed from the formers and subjected to a conventional halogenation procedure and then sprayed with a donning aid consisting of:

| Cetyl Pyridinium Chloride | 2% by weight |
|---|---|
| Lauric Acid | 2% by weight |
| Water | qs 100% |

The temperature of the spraying solution was 100° F. The gloves were then dried at 140° F. for 5 minutes.

The thus produced gloves exhibit good hand donning properties.

EXAMPLES 2–5

Example 1 was repeated except that the polymer solution consisted essentially of a 4% solution of GANTREZ ES 425 in industrial methylated spritis. The thus treated polymer gloves were subjected to the post treatments summarised in the following table.

| Example No | Halogenation | CPC/Lauric Acid |
|---|---|---|
| 2 | Yes | No |
| 3 | Yes | Yes |
| 4 | No | No |
| 5 | No | Yes |

The thus produced gloves exhibit good hand donning properties.

EXAMPLE 6

Examples 2–5 were repeated except that the polymer solution consisted of:

| GANTREZ 425 | 4.8% by weight |
|---|---|
| SCRIPTSET 550 | 1.2% by weight |
| Industrial Methylated Spirit | 94% by weight |

The gloves thus produced exhibited good wet and dry hand donning properties.

The surface morphology of gloves produced in accordance with Examples 3 and 6 was examined together with that of a control sample which is a conventional halogenated glove having no polymer treatment in accordance with the invention.

Surface roughness measurements and surface traces were obtained by surface profilometry using a Rank Taylor-Hobson TALLYSURF 10 profilometer.

Glove samples were taken from the middle finger of each glove for the control samples and the glove of Example 3 the amplification $(V_v)$ was ×5000 whereas (because of the increase in difference between the lowest and highest points of the probe) that for the glove for Example 6 was $V_v$=X1000. The $V_h$ setting was 0.8 mm (cut-off) in each case.

The surface roughness (averaged in three readings) was

| | |
|---|---|
| Example 3 | 0.55 μm |
| Example 6 | 2.92 μm |
| Control | 0.49 μm |

FIG. 1 in the accompanying drawing depicts the surface trace for each glove over a length of 3 cm ($V_h$ - ×10 and $V_v$ - ×1000).

EXAMPLE 7

The Application of Gantrez E5-425/Scripset 540 Coatings to Synthetic Latices The synthetic latices shown in table 1 below, were coagulation dipped, as described below, and coated with a solution (an industrial Methylated Spirits) of 2.8% by weight GANTREZ ES-425, 1.2% by weight SCRIPSET 540 and 0.8% by weight CARBOWAX 600 (referred to as 70/30 blend of Gantrez ES-425 and Scripset 540).

TABLE 1

| Sample No. | Polymer | Brand Name | Manufacturer |
|---|---|---|---|
| 1 | Polychloroprene | Neoprene 671 | Du Pont |
| 2 | Styrene butadiene Rubber | Revinex 26W10 | Doverstrand |
| 3 | Nitrile rubber | Revinex 99G41 | Doverstrand |
| 4 | Polyurethane | BIP L9009 | BIP |
| 5 | Polyurethane | Cydrothane HP5035 | Cyanamid |

Preheated (to 115° C.) ceramic glove formers were used to prepare coated latex gloves using the steps shown in Table 2. All the dipping operations were carried out by hand.

TABLE 2

| Process Details | Temperature | Time |
|---|---|---|
| Dip into coagulant[1] | 60° C. | Zero dwell |
| Air Dry | Room | 1 min |
| Dip into latex[2] | Room | 10 sec dwell |
| Air dry | Room | 1 min 30 sec |
| Dip into leach[3] | 70° C. | 2 min dwell |
| Air dry | Room | 1 min |
| Dip into coating[4] | room | zero dwell |
| Air dry | Room | 1 min |
| Oven dry | 115° C. | 30 min |

[1]the coagulant consisted of calcium nitrate, calcium carbonate powder and distilled water
[2]the latices were used in their as supplied form
[3]the leach consisted of distilled water
[4]the coating solution consisted of a 70/30 blend of Gantrez ES-425 and Scripset 540 dissolved in a 80/20 blend of Industrial Methylated Spirits (IMS) and Isopropyl alcohol (IPA). Samples were dipped only half way in the coating solutions.

Both the coated and uncoated latex surfaces were examined using optical microscopy. This revealed that roughened coatings were present on the synthetic latices. These roughened coatings, give rise to good damp hand donning performances.

EXAMPLE 8

The Application of a Range of Partly Esterified Maleic Anhydride Derived Polymers to Natural Rubber (NR) Latex The polymers listed below were applied onto coagulation dipped natural rubber latex surfaces.

1. Gantrez ES 225 (Acid primed latex)
2. Isopropyl half ester of Gantrez AN169
3. Propoxyethyl half ester of Gantrez AN169
4. n-Hexyl half ester of Gantrez AN169
5. n-Nonyl half ester of Gantrez AN169
6. n-Butyl half ester of polyethylene/maleic acid
7. SMA 2625

Preheated (to 115° C.) ceramic glove former were used to prepare samples using the procedure set out in Table 3 below. The dipping operations were carried out on the Cotswold Dipping Machine and Glove Coating Rig.

TABLE 3

| Process Details | Temperature | Time |
|---|---|---|
| Dip into coagulant[1] | 60 | zero dwell |
| Air dry | Room | 1 Min |
| Dip into latex[2] | Room | 12 sec |
| Air dry | Room | 1 min 30 sec |
| Dip into leach[3] | 70 | 2 Min |
| Air dry | Room | 1 Min |
| Dip into coating[4] | Room | 30 Sec |
| Air dry | Room | 1 Min |
| Oven dry | 115 | 30 Min |

[1]the coagulant consisted of calcium nitrate, calcium carbonate powder and distilled water.
[2]the latex used was as supplied Perry Style 42 or Dermaguard latex.
[3]the leach consisted of distilled water.
[4]the coating solutions used consisted of 4 to 6% polymer solids dissolved in Industrial Methylated Spirits.

Satisfactory hand donning characteristic results were obtained with the isopropyl half ester of Gantrez AN169 and with the n-butyl half ester of polyethylene/maleic acid. The other materials gave even better results

EXAMPLE 9

A glove former for moulding a surgeon's glove was dipped into Witco #A 127-71 polyurethane without coagulant. The resulting film was dried for 5 mins at 130° F. and then overdipped with an overdip formulation, comprising:

2.8% Gantrez ES-425

1.2% Scripset 540

0.8% Carbowax 600

Figures 2, 3:
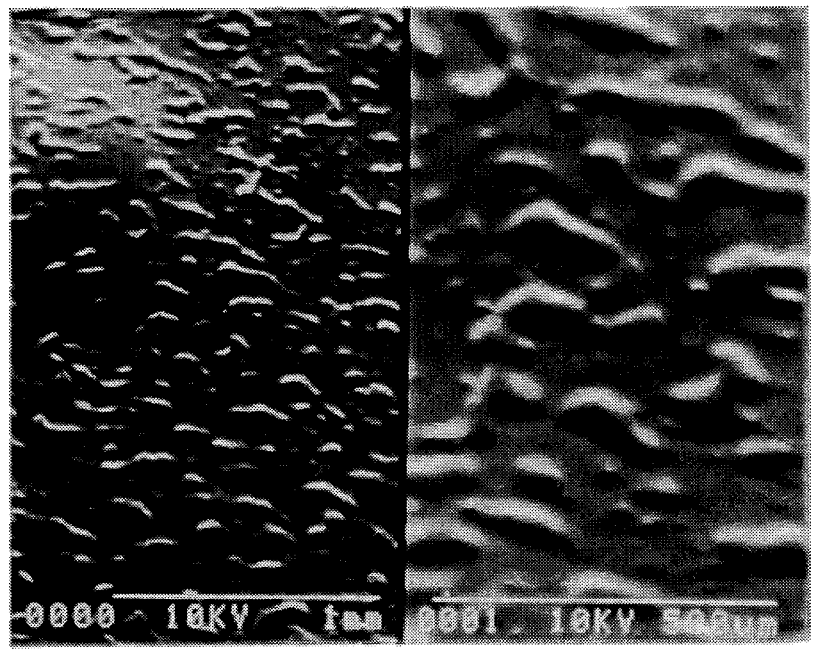
FIGS. 2–7 are photomicrographs of surfaces of gloves according to the invention.

Examination of the Gantrez-Scripset surface by Scanning electron microscope was carried out and the results are shown in FIGS. 2 (40 ×magnification) and 3 (100 ×magnification), from which is can be seen that domains were formed. The glove was found to exhibit good hand donning properties.

EXAMPLE 10

The process described in Example 9 was repeated, but using Du Pont Neoprene 571 latex instead of polyurethane and including an extra step of dipping the glove former in coagulant and drying it before dipping into the Neoprene latex.

Figures 4, 5:
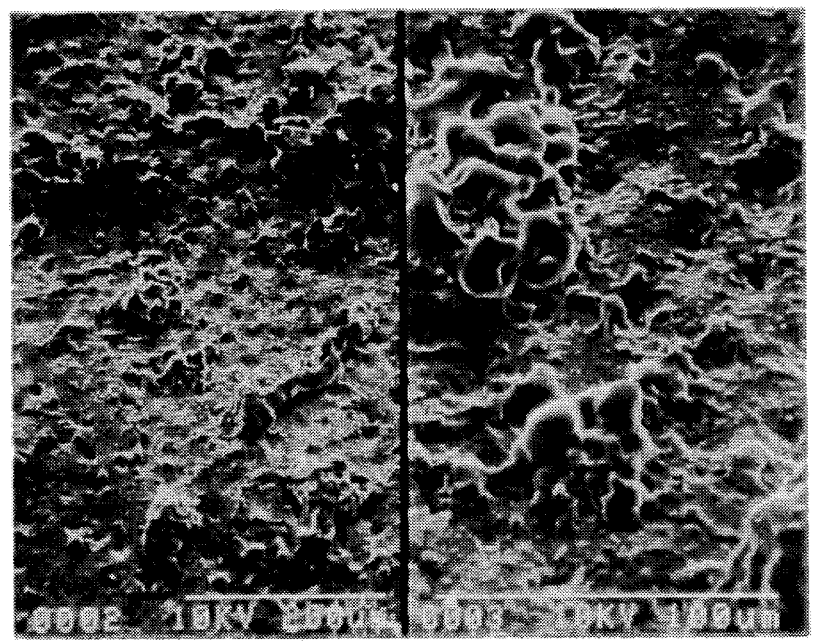

Examination of the Gantrez-Scripset surface by Scanning electron microscope was carried out and the results are shown in FIGS. 4 (150 ×magnification) and 5 (500 ×magnification), from which is can be seen that domains were formed. The glove was found to exhibit good hand donning properties.

EXAMPLE 11

The process described in Example 9 was repeated but using Reichhold Nitrile (TYLAC 68-060-00) latex instead of polyurethane and using 12 dips into the latex instead of 1. A further difference was that after drying the nitrile coating and before overdipping the sample was leached at 160° F. for 2 mins.

Figures 6, 7:
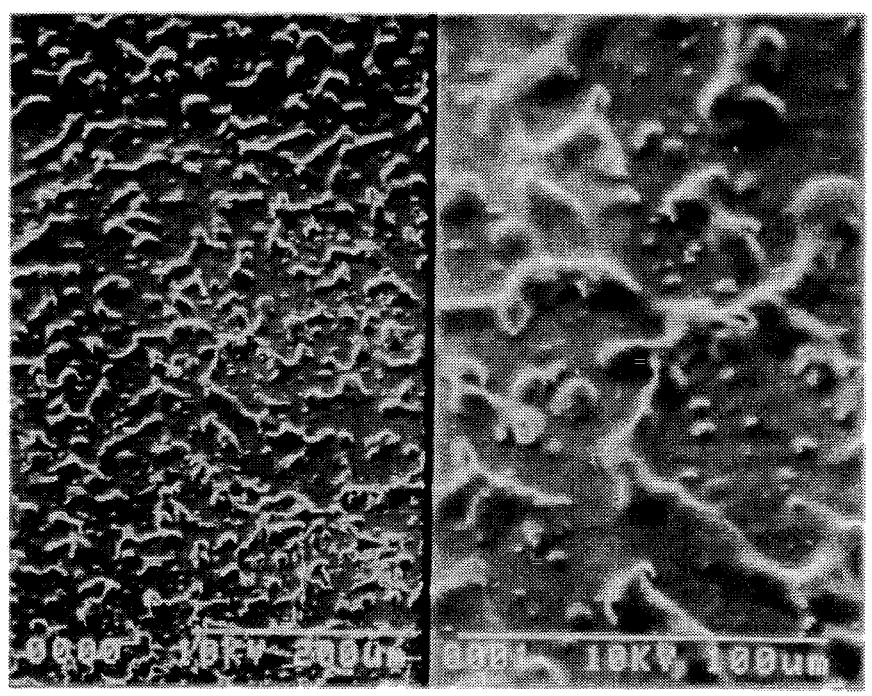

Examination of the Gantrez-Scripset surface by Scanning electron microscope was carried out and the results are shown in FIGS. 6 (150 ×magnification) and 7 (500 ×magnification), from which is can be seen that domains were formed. The glove was found to exhibit good hand donning properties.

Additional detail of some of the abovementioned coating polymers is given below:

Gantrez ES-225 and Half Esters of Gantrez AN169 are believed to contain repeating units of the formula:

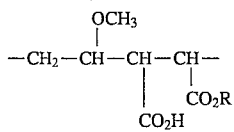

where R = (ie. Gantrez ES-255)
R = isopropyl
R = Propoxyethyl
R = n-pentyl    for the other half esters
R = n-hexyl
R = n-octyl
R = n-nonyl n-Butyl Half Ester of Poly/ethylene/maleic acid is believed to contain repeating units of the formula:

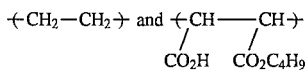

Scripset 540 and 550 and Butylated Scripset 520 are believed to contain repeating units of the formula:

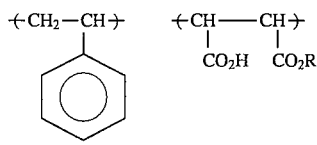

where
R=n-butyl (for Scripset 540)
R=ethyl/n-butyl mixture (for Scripset 550)
R=n-butyl (for Butylated Scripset 520)
for Butylated Scripset 520 the ratio of the number of the first units to the number of the second units is 1:1, Scripsets 540 and 550 the ratio is 1:<1.
SMA 2625
is believed to be

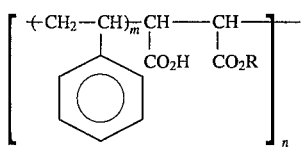

where
m=1 to 3 n=6 to 8
where R is a low alkyl group.

We claim:

1. A surgeon's glove having raised domains which improve the donning properties of the glove, said glove comprising a natural or synthetic elastomer, which has, on the hand contacting surface thereof, a layer comprising a polymer comprising repeating units of the formula (I):

or a polymer comprising repeating units of the formula (IA)

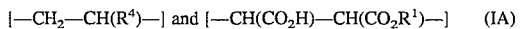

or a mixture of said polymers having repeating units of formulas (I) and (IA) wherein R is alkyl containing up to 9 carbon atoms, each $R^1$ is independently alkyl containing up to 9 carbon atoms or an alkoxy alkyl group containing up to four carbon atoms in the alkoxy part and up to four carbon atoms in the alkyl part, and $R^4$ is hydrogen or phenyl; and wherein the thickness of the polymer layer at the domains is up to 25 μm thicker than the thickness of the polymer layer in the remaining areas of the glove.

2. A glove according to claim 1 wherein R is a methyl group and $R^1$ is an alkyl group having from one to nine carbon atoms.

3. A glove according to claim 2 wherein $R^1$ is a $(CH_2)_2CH_3$ group.

4. A glove according to claim 1, wherein said elastomer comprises a member selected from the group consisting of natural rubber, a polychloroprene, a nitrile rubber, a styrene butadiene rubber and a polyurethane.

5. A glove according to claim 1, wherein the polymer layer is continuous.

6. A glove according to claim 1, which is comprised of rubber and which has, on the hand contacting surface thereof, a layer comprising a polymer comprising repeating units of the formula:

where $R^1$ is an alkyl group having from one to nine carbon atoms.

7. A glove according to claim 1, wherein said layer of polymer comprises a mixture of said polymers of formulas (I) and (IA), wherein R is methyl, each $R^1$ is independently alkyl containing up to nine carbon atoms, and $R^4$ is phenyl.

8. A glove according to claim 1, wherein said layer of polymer comprises a mixture of said polymers of formulas (I) and (IA), wherein R is methyl, $R^1$ in formula (I) is ethyl, $R^1$ in formula (IA) is n-butyl and $R^4$ is phenyl.

* * * * *